United States Patent
Powell

(10) Patent No.: US 10,453,563 B2
(45) Date of Patent: Oct. 22, 2019

(54) HEALTH CARE EVENT MATCHING

(71) Applicant: IMS Health Incorporated, Danbury, CT (US)

(72) Inventor: David Powell, Staffordshire (GB)

(73) Assignee: IMS Health Technology Services Limited, London (GB)

(*) Notice: Subject to any disclaimer, the term of this patent is extended or adjusted under 35 U.S.C. 154(b) by 621 days.

(21) Appl. No.: 14/541,432

(22) Filed: Nov. 14, 2014

(65) Prior Publication Data

US 2016/0140295 A1 May 19, 2016

(51) Int. Cl.
| | |
|---|---|
| G16H 10/60 | (2018.01) |
| G06F 16/28 | (2019.01) |
| G06Q 10/06 | (2012.01) |
| G06Q 10/10 | (2012.01) |
| G16H 50/20 | (2018.01) |
| G16H 50/30 | (2018.01) |
| G16H 50/70 | (2018.01) |
| G06Q 50/24 | (2012.01) |

(52) U.S. Cl.
CPC .......... *G16H 10/60* (2018.01); *G06F 16/288* (2019.01); *G06Q 10/06* (2013.01); *G06Q 10/10* (2013.01); *G16H 50/20* (2018.01); *G16H 50/30* (2018.01); *G16H 50/70* (2018.01); *G06Q 50/24* (2013.01)

(58) Field of Classification Search
CPC .............................. G06Q 50/22; G06Q 50/24
See application file for complete search history.

(56) References Cited

U.S. PATENT DOCUMENTS

| | | | |
|---|---|---|---|
| 5,917,489 A | 6/1999 | Thurlow et al. | |
| 6,643,648 B1 * | 11/2003 | Ross | G06F 21/6227 707/695 |
| 2004/0153435 A1 * | 8/2004 | Gudbjartsson | G06F 17/30595 |
| 2013/0144816 A1 | 6/2013 | Smith et al. | |
| 2014/0074509 A1 | 3/2014 | Amarasingham et al. | |
| 2014/0372147 A1 | 12/2014 | White | |

FOREIGN PATENT DOCUMENTS

WO  WO 99/33390  7/1999

OTHER PUBLICATIONS

Wang, X., & Ling, J. (0001). Multiple valued logic approach for matching patient records in multiple databases. Journal of Biomedical Informatics, doi:http://dx.doi.org/10.1016/j.jbi.2011.10.009 (Year: 2011).*
Extended European Search Report in European Application No. 15194672.0, dated Mar. 14, 2016, 9 pages.

* cited by examiner

*Primary Examiner* — Lena Najarian
(74) *Attorney, Agent, or Firm* — Fish & Richardson P.C.

(57) ABSTRACT

A computer-implemented method includes generating a matching rule defined by a user, where the matching rule is a clear text rule, and receiving a transaction message that includes patient data from one or more health care facilities, where the patient data includes one or more patient health care events. A custom extension to a relational database is generated based on the received patient data, and the generated matching rules is applied to the received patient data at the custom extension to the relational database. Related patient event records within the custom extension to the relational database are identified and the related patient event records are configured based on the applied matching rule.

18 Claims, 5 Drawing Sheets

HEALTH CARE EVENT MATCHING

BACKGROUND

Health care organizations often wish to link patient health care events together for a variety of different reasons.

SUMMARY

In one aspect, a computer-implemented method includes generating a matching rule defined by a user, where the matching rule is a clear text rule, and receiving a transaction message that includes patient data from one or more health care facilities, where the patient data includes one or more patient health care events. A custom extension to a relational database is generated based on the received patient data, and the generated matching rule is applied to the received patient data at the custom extension to the relational database. Related patient event records within the custom extension to the relational database are identified, and the related patient event records are configured based on the applied matching rule.

In another aspect, a request to update a matching rule is received from the user, the related patient event records are updated based on the updated matching rule, and the related patient event records are presented to the user. In yet another aspect, identifying related patient event records within the custom extension to the relational database include identifying patient events related to a particular patient identifying attribute.

In another aspect, identifying related patient event records within the custom extension to the relational database includes identifying patient events related to the treatment of a particular diagnosis. In yet another aspect, identifying related patient event records within the custom extension to the relational database includes identifying patient events related to a particular patient event attribute.

In another aspect, identifying related patient event records within the custom extension to the relational database includes identifying patient events that exhibit a particular risk. In yet another aspect, the matching rule is a unique matching rule that is not specific to a software program language. In another aspect, receiving a transaction message that includes patient data from one or more health care facilities includes receiving a data file, a stream of data, or a datagram.

In yet another aspect, the patient data may further include patient attributes selected from the group consisting of age, sex, address, diagnosis, specialty, diagnostic test, date of event, pharmaceutical drug prescription, and outcome of a patient event. In yet another aspect, configuring the related patient event records based on the applied matching rule includes tagging the related patient event records with an identifier.

DETAILED DESCRIPTION

Figure 1:
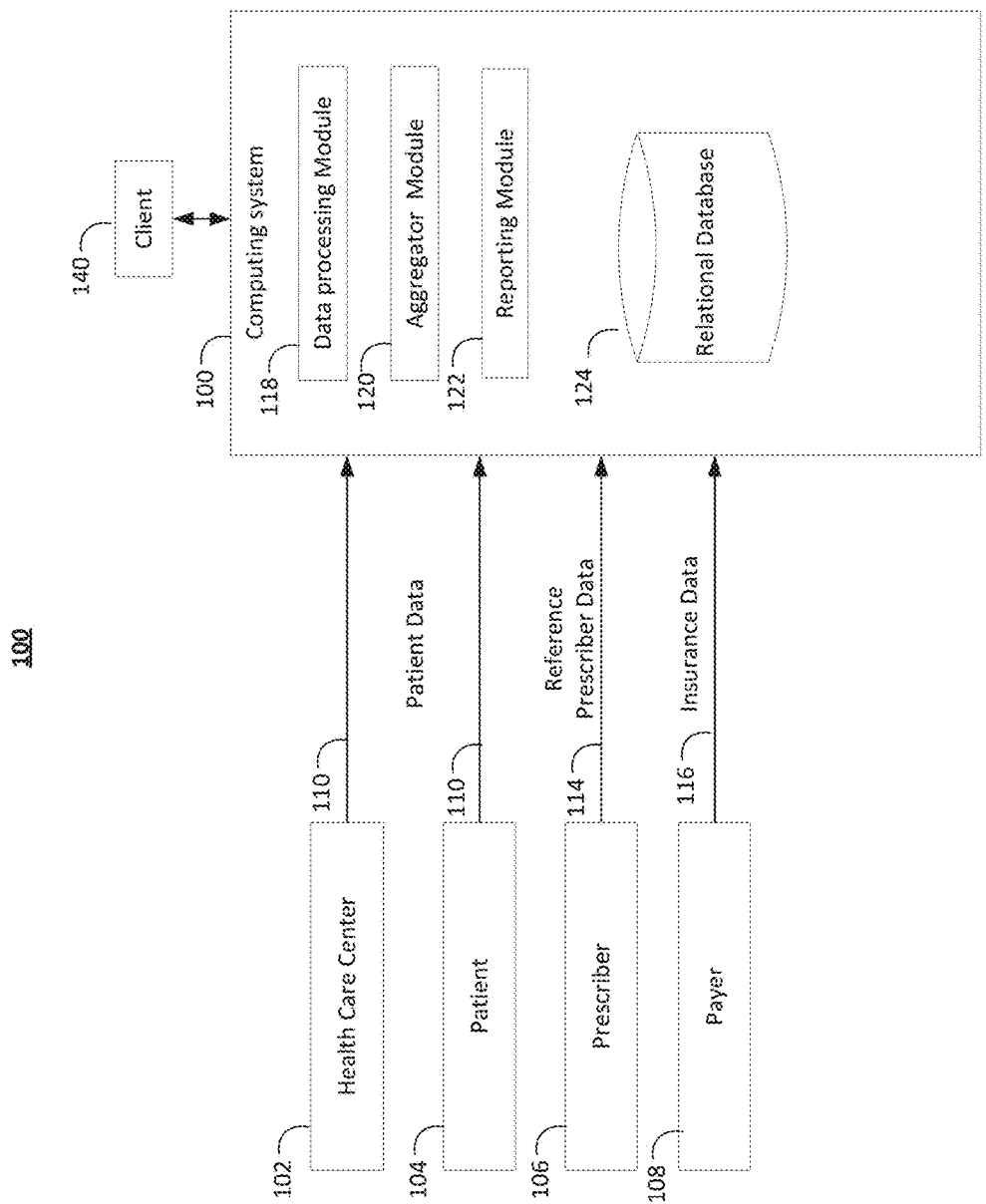
FIG. 1 illustrates an example of an analytical infrastructure implemented in a computing system 100.

This disclosure generally describes computer-implemented methods, software, and systems for implementing matching algorithms for the linking of health care events. The computer-implemented methods, systems, and software provide a web-based interactive tool for implementing the one or more matching algorithms. The web-based interactive tool for implementing the one or more matching algorithms may be used by one or more information technologist at healthcare organizations. The web-based interactive tool may be used to link patient health care events together to analyze patient care pathways, to identify patient events which may exhibit a risk, and/or to identify patient events that may require clinical investigation.

A patient pathway is a sequence of events that a patient may experience for the treatment of a particular medical condition. These events may include medical procedures, diagnoses, or medical test results. A treatment event may be an outpatient attendance, an attendance of a hospital appointment, an attendance of a screening, an in-patient stay, a pathology test, or any other suitable health event. Health care events may contains patient details, such as, age, sex, and address, any diagnosis, the procedure conducted during the event, and/or the outcome of the event. A user at a health care organization may link health care events together to identify and analyze patient health care pathways. The linked health care data may include the one or more treatment events a particular patient was involved in for the treatment of his/her particular medical condition. The user may compare the one or more treatment events for a particular patient to the one or more treatment events for a second patient with the same medical condition. Monitoring the different treatment pathways experienced by different patients for the treatment of the same condition can be used to identify the variations in the treatment. This may provide insight into both the cost and clinical effectiveness of a specific pathway. Identifying an effective pathway for the treatment of a particular condition may potentially lead to the development of standardized care pathways for specific conditions. The linked health care date may be used to identify the one or more patient events that exhibit a particular risk characteristic. For example, a user at a health care organization may wish to identify the patients that may have a high risk of early death during a heart transplant. A user at a health care organization may wish to link patient events together to identify the patient events that may require clinical investigation. For example, the user may wish to identify all early deaths related to a specific medical condition and drug prescription.

Traditionally, health care organizations record and store patient treatment events as discrete patient events in large databases. Matching health care events together may include implementing matching rules within software code in a programming language such as Java, C, C++, C#, or any other suitable programming language, or within database procedures implemented using PL-SQL, T-SQL, SSIS, or SQL. The matching rules may require modification, in response to a change in requirement over time, or because different organizations utilize different matching policies. Implementing changes to matching rules may involve the use of a software or database developer which would be both time consuming. The present disclosure facilitates the linking of health care events based on pre-determined matching criteria or rule base in a more flexible and cost-effective manner that what has been traditional done by health care organizations. The invention separates the event matching rules from the software framework which performs the matching process. The matching rules are expressed in a unique and intuitive clear-text form. The matching characteristics may be modified by user without programming expertise, and without the need to change the software code.

FIG. 1 illustrates an example analytical infrastructure system implemented in a computing system 100. The computing system may be implemented as a data processing apparatus that is capable of providing the functionality discussed herein, and may include any appropriate combination of processors, memory, and other hardware and software that can receive appropriate medical data and process the data as discussed below. At a high-level, the illustrated example computing system 100 receives patient data from various institutes that provide healthcare to patients. The health care institutes may include hospitals, health care centers, and managed care organizations. In some implementations, pharmaceutical prescription information may be received from pharmacies that dispense medication to patients. It is important to understand that the system may be configured to preserve patient privacy and will not store nominative data in an aggregated database, but only de-identified data.

The patient data, the prescriber data, and insurance data received at the computing systems data sources may be integrated and stored at a custom extension to a relational database at the computing systems of the analytical infrastructure. The custom extension database may be an extension to one or more relational databases that store the patient data, prescriber data, and insurance data. The custom extension to the relational database may be a computational database. The custom extension to the relational database may have the processing capability to execute extensive computations and calculations. The custom extension to the relational database may perform extensive calculations and computations at high processing speeds. The custom extension to the relational database may be an energy efficient and time efficient database. The data at the custom extension may be structured so that data may be retrieved and processed in a meaningful time frame. The data may be structured to reduce the bandwidth necessary to communicate the data over an internet connect or the like.

The patient data 110 may include patient identifying data, for example, the patient data may include the name, gender, age, and address for patients treated at the health care institutes. The patient data may also include patient event data. As described earlier, a patient event may be an outpatient attendance, an attendance of a hospital appointment, an attendance of a screening, an in-patient stay, a pathology test, or any other suitable health event. This data may be provided to the computing system 100 on a daily basis. In other implementations, the patient event data is provided to the computing system 100 monthly.

The longitudinal patient data 112 may include sanitized retail patient-level data for the one or more patient systems 104. For example, the longitudinal patient data 112 may include information about retail pharmacy-sourced prescription insurance claims, retail pharmaceutical scripts, and/or patient profile data. Longitudinal patient data 112 includes information about aspects of care for the one or more patient systems 104. Though FIG. 1 illustrates the longitudinal patient data 112 as being received by the computing system 100 directly from one or more patient systems 104, the longitudinal patient data 112 may be collected by one or more other systems and then provided to the computing system 100 in a manner analogous to the similar approach discussed for consumption data 110. Moreover, the longitudinal patient data 112 may not originate from the one or more patient systems 104, but may rather be provided by one or more prescribers/physicians with whom the patient interacts, insurance companies to which a patient submits insurance claims, and/or retailers at which a patient purchases a pharmaceutical product. In some implementations the longitudinal patient data 112 may originate from one or more pharmaceutical companies.

The reference prescriber data 114 may include detailed data about health care providers and physicians. The reference prescriber data may include details such as the specialty of a physician, the IDN affiliation of a physician, and/or the health insurance network that the physician may be associated with. This data may be obtained through prescriptions written by the particular prescribing physician. Though FIG. 1 illustrates the reference prescriber data 114 as being received by the computing system 100 directly from one or more prescriber systems 106, the reference prescriber data 114 may be collected by one or more other systems and then provided to the computing system 100 in a manner analogous to the similar approach discussed for retail consumption data 110. Moreover, the reference prescriber data 114 may not originate from the one or more prescriber systems 106, but rather be created and/or maintained by one or more other entities (e.g., government agencies or professional medical organizations) that track information about the prescribing behavior of prescribers 106.

The insurance data 116 may include information about insurance companies covering the cost of prescriptions. For example, the insurance data 116 may include information about how much of a prescription's cost was covered by the insurance company or by Medicaid. Though FIG. 1 illustrates the insurance data 116 as being received by the computing system 100 directly from one or more payer system 108, the insurance data 111 may be collected by one or more other systems and then provided to the computing system 100.

For illustrative purposes, computing system 100 will be described as including a data processing module 118, an aggregator module 120, a reporting module 122, and a relational database 124. However, the computing system 100 may be any computing platform capable of performing the described functions. The computing system 100 may include one or more servers that may include hardware, software, or a combination of both for performing the described functions. Moreover, the aggregator 120 and the relational database 124 may be implemented together or separately in hardware and/or software.

One or more clients 140 may interface with the computing system 100 to request search queries of the relational database of pathway shapes. In some implementations, the one or more clients 140 may include a web browser that provides Internet-based access to the computing system 100. Through the web browser, a user of a client 140 (e.g., a wholesaler, a retail outlet, a health information analyst, or a prescriber) may perform a pathway analytical query.

There may be any number of clients 140 associated with, or external to, the example computing system 100. While the illustrated example computing system 100 is shown in communication with one client 116, alternative implementations of the example computing system 100 may communicate with any number of clients 116 suitable to the purposes of the example computing system 100. Further, the term "client" and "user" may be used interchangeably as appropriate without departing from the scope of this disclosure. Moreover, while client 140 is described in terms of being used by a single user, this disclosure contemplates that many users may share the use of one computer, or that one user may use multiple computers.

The illustrated client 140 is intended to encompass computing devices such as a desktop computer, laptop/notebook computer, wireless data port, smartphone, personal digital assistant (PDA), tablet computing device, one or more processors within these devices, or any other suitable processing device. For example, the client 116 may include a computer that includes an input device, such as a keypad, touch screen, or other device that can accept user information, and an output device that conveys information associated with the operation of the computing system 100. The input device may be used by client 140 to provide instructions to computing system 100 that computing system 100 can execute to provide query results requested by client 140 from the various data that computing system 100 receives.

Figure 2:
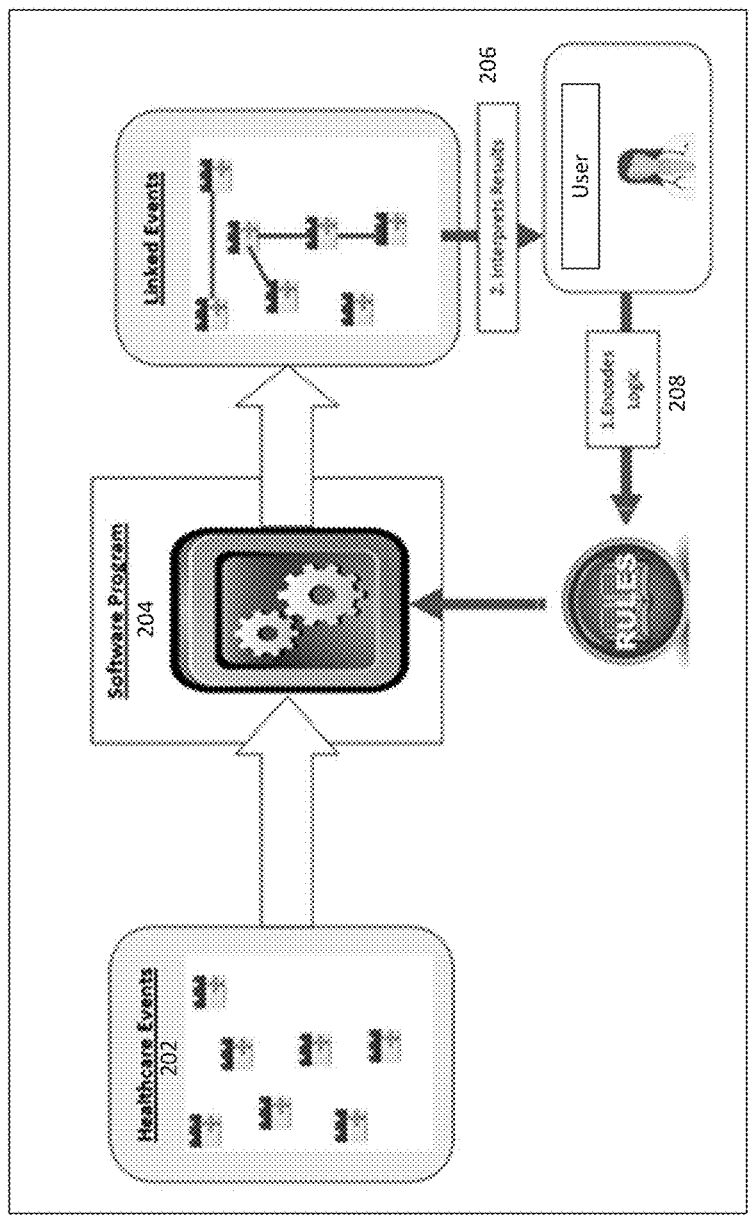
FIG. 2 is a diagram describes the process of updating one or more matching rules.

FIG. 2 is a flow diagram that describes the process for updating one or more matching rules. The health care events data may be received at received at a server system (202). The health care events may be received from the computing systems of one or more health care facilities. The health care facilities may include health centers, hospitals, and managed care organizations. A patient event may be an outpatient attendance, an attendance of a hospital appointment, an attendance of a screening, an in-patient stay, or a medical test. The heath care events may be received as discrete patient events. The patient event may include details of the subject of the patient event. The patient event data may include de-identified patient data. The server system may be configured to preserve patient privacy. The patient data may include personal patient attributes, for example, age, sex, and/or address. The discrete patient events may be stored at one or more databases at the server system. In some implementations, the discrete patient events may be stored at a custom extension to a relational database.

The discrete health care events may be linked together (204). The linked patient events may be interpreted by a user (206). The patient events may be linked together based on the patient events for a particular patient. The linked patient events for a particular patient may represent the care pathway data for the specific condition. The server system may generate a pathway shape for patient events for the treatment of a specific condition. This pathway shape may be stored as a unique value as care pathway data. The care pathway data for the specific condition may be generated by linking the one or more patient events related to the treatment of the specific condition. The server system may generate an event shape for each patient event in the care pathway for the treatment of a specific condition. The server system may then aggregate the event shapes for the string of patient events to form a pathway shape. This pathway shape may be stored as a unique value as care pathway data. The patient events may be linked based on patient events that exhibit a particular risk characteristic. The server system may identify one or more patients with a particular risk characteristic and link the patient events associated with each of the one or more patients. The patient events may be linked based on patient events that may require clinical investigation. The patient events may be linked based on any other suitable criteria.

The user may be an information technologist at a health care institute that is interested in the trends that occurs across patient care. The user may analyze the linked patient events data stored at the server system. In some implementations, the user may access the linked patient events through a web-based interactive tool. The user may analyze the linked events and recognize that the one or more matching rules used to link the patient events may need to be changed. In some implementations, the server system may prompt a user to update the matching rules on a cycle. For examples, the server system may prompt the user to update the matching rules every six months or any other suitable time period. In some implementations, the matching rules may require modifications based on changes in requirements. The user encodes logic to the linked events to update the one or more matching rules (208). The user may utilize one or more intuitive clear text form that is not specific to a programming language to modify the one or more matching rules previously used to link the patient events.

Figure 3:
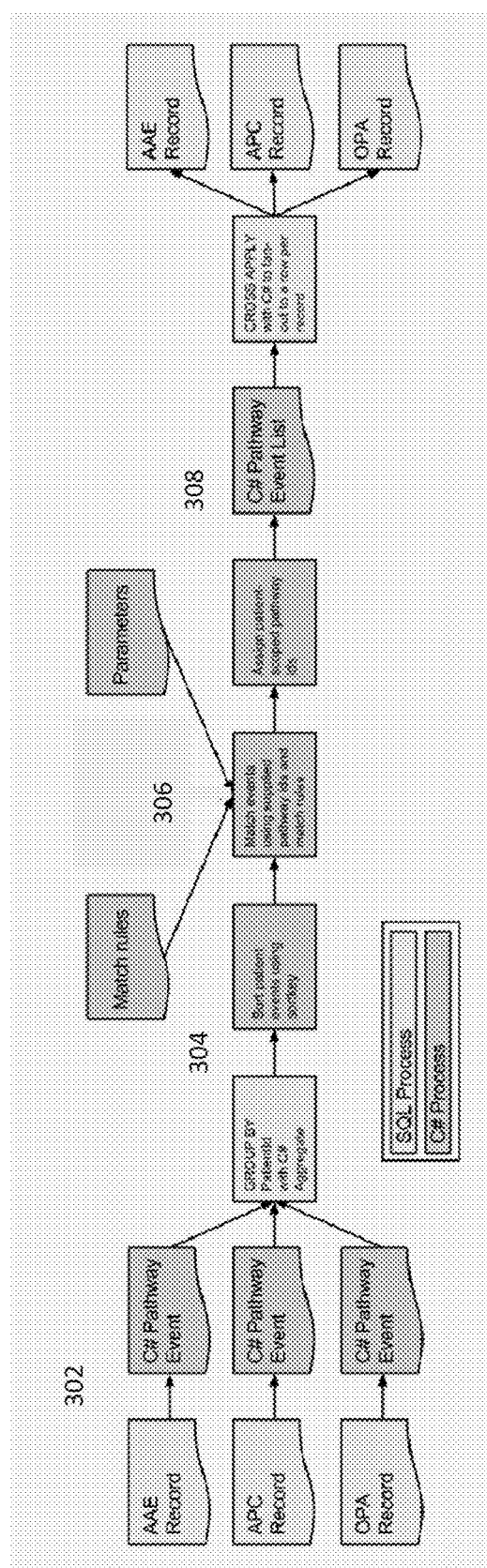
FIG. 3 is an illustration of one implementation of matching related patient events.

FIG. 3 is an illustration of one implementation of matching related patient events. The server system receives one or more discrete patient heath care events (302). The discrete patient events may be received as an electronic transaction message at the server system. For the example illustrated in FIG. 3, the server system may receive three discrete patient events, an accident and emergency patient event (AAE), an admitted patient care record (APC), and an outpatient attendance record (OPA). The received patient events may be received from one or more different health care centers. The patient events may be received as one or more transaction messages from the computing systems at one or more health care facilities. The received discrete one or more patient events are grouped together with a C# aggregate with a patient identifier (304). The grouped patient events, with the patient identifier, populate the fields of a custom extension database to a relational database. The patient events may be sorted by a sort key. The sort key may be a dated sort key that sorts the patient events by the date of the event. In some implementations, the sort key may sort patient events by date and time of the event.

The server system may match the patient events based on the matching rules and pathway identifiers (306). The matching rules may be a user defined rule. The matching rule may be a clear text rule that is not specific to a programming language. The matching rule may be a logic rule that when implemented groups patient events that share common characteristics together. A matching rule may be used to group together patient events for a specific patient to identify a patient pathway. The patient pathway may identify the patient events involved with the treatment of the patient condition. The user may define another matching rule that may be used to group together patient events that may exhibit a particular risk characteristic. The user may define another matching rule that may be used to identify patient events that may require clinical investigation. The user may define any number of matching rules to execute on the received patient events. The user may alter one or more matching defined matching rules. The defined matching rules may be stored at a custom extension to the relational database.

The server system may identify the related patient events based on the applied matching rule and may assign an identifier to the related patient events (308). The identifier may be a numeric identifier, the identifier may be an alphanumeric identifier. In some implementations, the identifier may be associated with each of the related patient events. The identifier may be associated with each discrete patient event of the related patient events. In some implementations, one identifier may be associated with a group of related patient events. In some implementations, the identifier may be a computer generated binary identifier. In some implementations, the identifier may be a user generated code that is used to tag the related patient events. In some implementations, the related patient events may be stored as a single record at the custom extension to the relational database. In some implementations, the single record of related patient events may be stored at a one or more databases associated with the server system.

Figure 4:
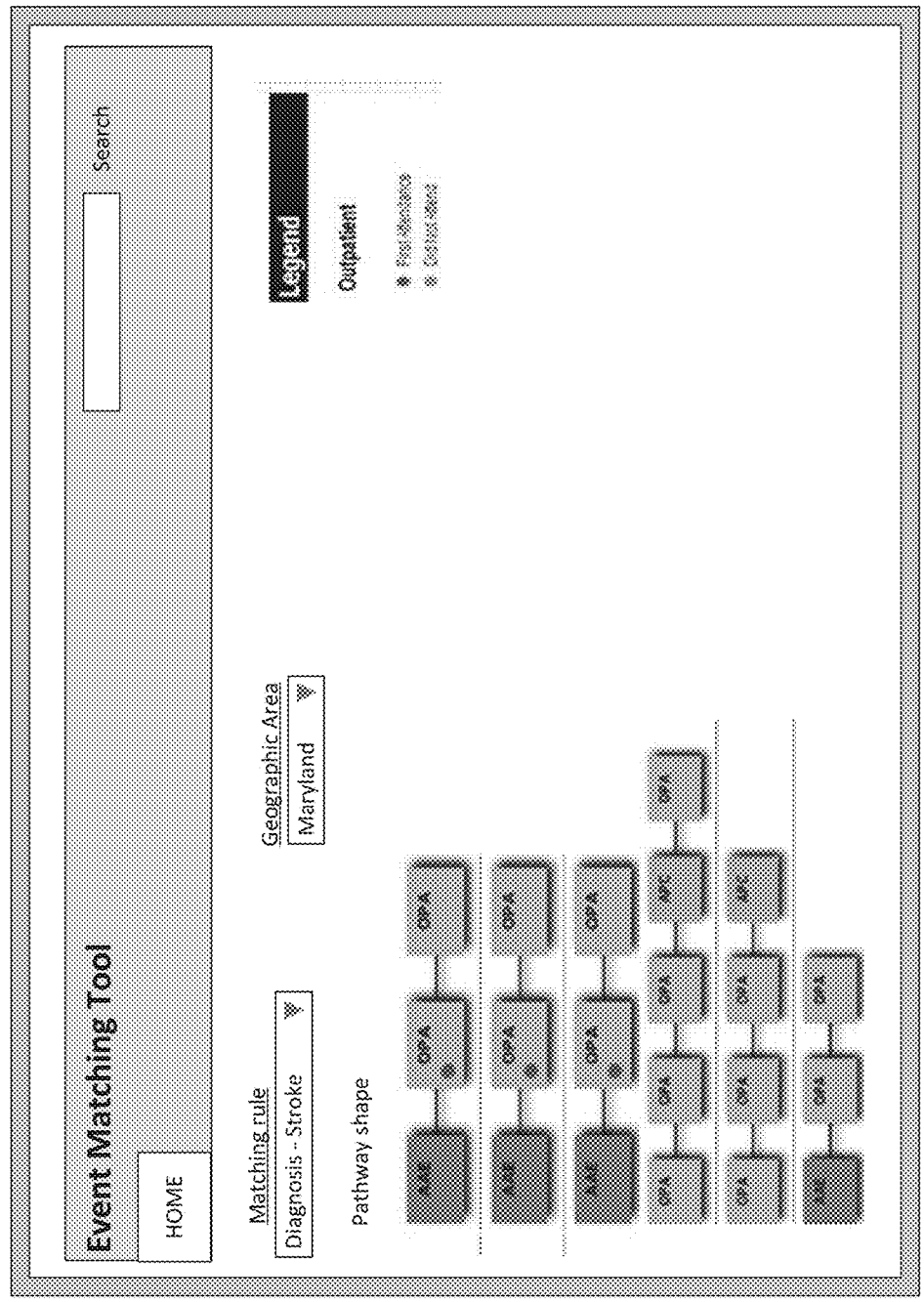
FIG. 4 illustrates an example user interface for user interaction with a web-application of an event matching offering.

FIG. 4 illustrates an example user interface for user interaction with a web-application of an event matching offering. The user interface 400 may be displayed when a user logs into a secure connection with the event matching offering. The event matching offering may be used by an information technologist at a health care institute. The user may define one or more matching rules using clear text rules. The user may select a matching rule to apply to the received patient data. For the example illustrated in FIG. 4, the user may select to apply the matching rule based on a stroke diagnosis. The computing systems at the analytical infrastructure may field and or mine the patient data at the relational database to identify patient events that are related to the treatment of a stroke diagnosis. In some implementations, the user may specify the related events based on treatments within a particular geographic location. For the example illustrated, the user may specify patient events in Maryland State. The computing systems at the analytical infrastructure may present, to the user, the care pathway for one or more patients with the selected diagnosis.

Figure 5:
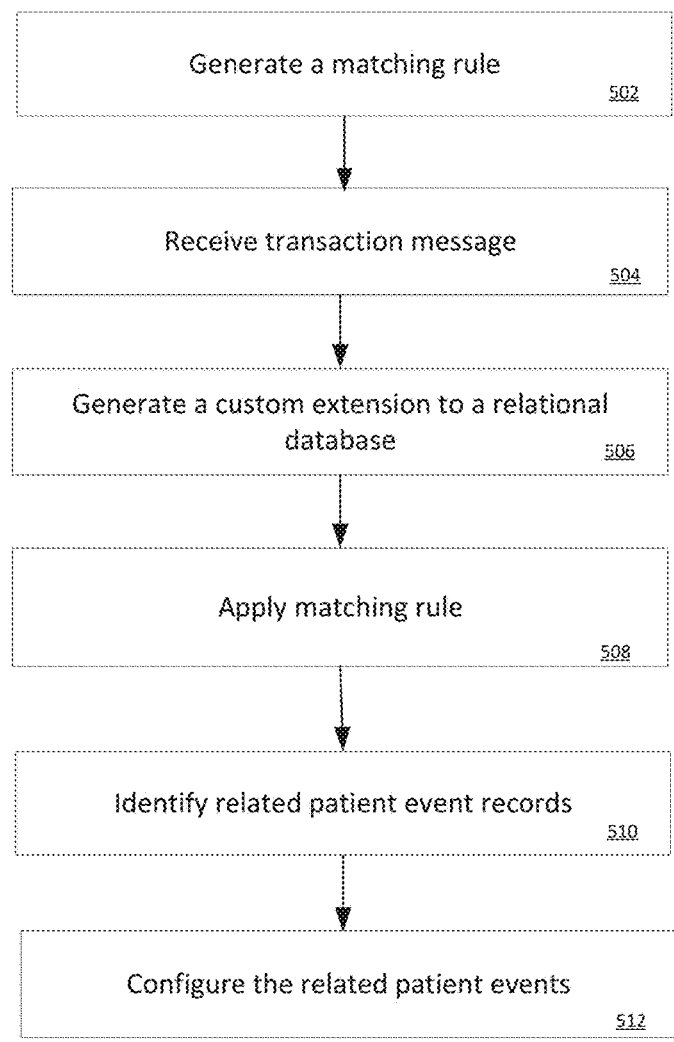
FIG. 5 is a flow chart of an example process for configuring related patient event records.

FIG. 5 is a flow chart of an example process for configuring related patient event records. The computing systems at the analytical infrastructure generates a matching rule defined by a user (502). The user may be an information technologist at a health care institute that is interested in the trends that occurs across patient care. The matching rule may be a clear text rule that may be easily interpreted by non-programmer users. The clear text matching rule is not specific to any one programming language. In some implementations, the matching rule may be applied to any programming language protocol. The matching rule may be defined to implement logic to group patient events together that identify a patient pathway for a particular patient. The matching rule may be defined to implement logic to group patient events that may exhibit a particular risk. The matching rule may be defined to implement logic to group patient events that may require clinical investigation. The matching rule may be stored at one or more databases associated with the computing systems at the analytical infrastructure. For example, the matching rule may be stored as a custom extension to a relational database at the analytical infrastructure.

The computing systems at the analytical infrastructure receives a transaction message that includes patient data from one or more health care facilities (504). The transaction message received may be a data file, a stream of data, or a datagram. The transaction message may be an electronic transaction message. The electronic transaction message may be received by one or more processors of the computing systems at the analytical infrastructure. The patient data may be collected at one or more processors associated with the one or more health care facilities. The health care facilities may include health centers, hospitals, and managed care organizations. In some implementations, the patient data from the one or more processors may be communicated, as an electronic transaction message, to the computing systems at the analytical infrastructure on a periodic basis. For example, the patient data may be received at the computing systems of the analytical infrastructure daily, weekly, monthly or quarterly. The patient data may be received at any suitable time period.

The patient data received from the one or more health care facilities may include one or more patient health care events. The patient data received may be de-identified patient data. The patient data may be include patient attribute details, for example, sex, age, address, diagnosis, one or more patient events, the dates of the one or more patient events, and the outcome of the one or more patient events. The patient data may further include data that is associated with the physician that cared for the patient. For example, the patient data may include the physician specialty, and the pharmaceutical prescription. The patient data may be tagged with one or more patient identifiers that identify the patient associated with the patient data.

The computing systems at the analytical infrastructure generates a custom extension to a relational database based on the received patient data (506). The received patient data may be used to populate the custom extension to the relational database. The custom extension to the relational database may be updated based on the patient data received on a periodic basis. The updated custom extension to the relational database may have the processing capability to execute extensive computations and calculations. The custom extension to the relational database may perform extensive calculations and computations high processing speeds. The custom extension to the relational database may be an energy efficient and time efficient database. The computing systems at the analytical infrastructure applies the generated matching rule to the received patient data at the custom extension to the relational database (508). One or more processors of the computing systems at the analytical infrastructure may implement the logic rules defined by the matching rule to identify the one or more related patient health care events from the patient data at the updated custom extension to the relational database. The custom extension to the relational database may have the ability to apply the matching rule at high speeds. The related patient health care events may be mined from large data sets and be identified at high speeds.

The computing systems at the analytical infrastructure identifies related patient event records within the custom extension to the relational database (510). The one or more processors of the computing systems at the analytical infrastructure may implement the logic defined by the matching rule to identify the related patient events. In some implementations, where the matching rule is defined to group patient events together that identify a patient pathway for a particular patient, the one or more processors may field and/or mine the patient data to identify patient events that may be tagged with similar patient identifiers. In some implementations, the matching rule may be configured to identify patient events associated with a patient identifying attribute. For example, the matching rule may be configured to identify patient events associated with patients of a particular age, sex, or address. In some implementations, where the matching rule is defined to group patient events that may exhibit a particular risk, the one or more processors may field and or mine the patient data to identify patient events that are associated with the particular risk. For example, the matching rule may be defined to identify patients that may be at high risk of early death during a heart transplant. In some implementations, where the matching rule is defined to group patient events that may require clinical investigation, the one or more processors may field and or mine the patient data to identify early death related to a specific condition and drug prescription. In some implementations, the matching rule may be defined to identify patient events related to a particular patient event attribute. For example, the matching rule may be defined to identify patient events related to an operational procedure, an MRI event, or a co-morbidity event.

The computing systems at the analytical infrastructure configures the related patient event records based on the applied matching rule (512). The one or more processors of the computing systems at the analytical infrastructure may tag the one or more patient events that are identified as related events. In some implementations, the related patient events may be grouped together and a single tag is appended to the grouped patient events. The grouped patient events may be stored at one or more databases at the analytical infrastructure. In some implementations, each of the discrete patient events that are related are tagged with an identifier.

Implementations of the subject matter and the functional operations described in this specification can be implemented in digital electronic circuitry, in tangibly-implemented computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible non-transitory program carrier for execution by, or to control the operation of, data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including, by way of example, a programmable processor, a computer, or multiple processors or computers. The apparatus can also be or further include special purpose logic circuitry, e.g., a central processing unit (CPU), a FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example Linux, UNIX, Windows, Mac OS, Android, iOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a central processing unit (CPU), a FPGA (field programmable gate array), or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or GUI, may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN), a wide area network (WAN), e.g., the Internet, and a wireless local area network (WLAN).

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of sub-combinations.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be helpful. Moreover, the separation of various system modules and components in the implementations described above should not be understood as requiring such separation in all implementations, and it should be understood that the described program components and systems can generally be integrated together in a single software product or packaged into multiple software products.

Particular implementations of the subject matter have been described. Other implementations, alterations, and permutations of the described implementations are within the scope of the following claims as will be apparent to those skilled in the art. For example, the actions recited in the claims can be performed in a different order and still achieve desirable results.

Accordingly, the above description of example implementations does not define or constrain this disclosure. Other changes, substitutions, and alterations are also possible without departing from the spirit and scope of this disclosure.

The invention claimed is:

1. A computer-implemented method comprising:
generating, by a server system, a user-defined matching rule, wherein:
the matching rule is expressed in a clear-text format not specific to a programming language;
the matching rule is configured to be modified by a user without modifying a programming language used to encode data stored in one or more databases of the server system, and
the matching rule specifies one or more predetermined matching criteria for identifying related patient health care events from among multiple patient health care events for a plurality of patients;
receiving, by the server system, a first transaction message from a first computer system, wherein:
the first transaction message includes de-identified patient data obtained from a first healthcare facility, and
the first transaction message specifies a first set of patient health care events included within the de-identified patient data;
receiving, by the server system, a second transaction message from a second computer system, wherein:
the second transaction message includes de-identified patient data obtained from a second healthcare facility, and
the second transaction message identifies a second set of patient health care events included within the de-identified patient data;
determining, by the server system, that a first patient event identified within the first transaction message corresponds to a second patient event identified within the second transaction message based on the matching rule;
generating a custom extension to the one or more databases of the server system based on the de-identified patient data obtained from the first and second healthcare facilities;
generating, by the server system and within the custom extension to the one or more databases of the server system, a tag that associates the first patient event and the second patient event as related patient events;
appending, by the server system, the tag to a first set of data fields from the first computer system that are associated with the first patient event;

appending, by the server system, the tag to a second set of data fields from the second computer system that are associated with the second patient event;

generating, by the server system, an aggregate data record that includes (i) de-identified patient data corresponding to the first set of data fields and the second set of data fields and (ii) care pathway data linking the first set of data fields and the second set of data fields as a unique value for the related patient events; and storing, by the server system, the aggregate data record within the custom extension to the one or more databases of the server system.

2. The method of claim 1 further comprising:

receiving, by the server system and from a computing device of a user, a request to update at least one of the one or more predetermined matching criteria of the matching rule; and updating, by the server system, the de-identified patient data within the aggregate data record according to the at least one updated predetermined matching criteria.

3. The computer-implemented method of claim 1 wherein determining that the first patient event identified within the first transaction message corresponds to the second patient event identified within the second transaction message comprises:

determining a patient identifying attribute included within each of the first transaction message and the second transaction message; and determining that the first patient event identified within the first transaction message and the second patient event identified within the second transaction message correspond to the patient identifying attribute.

4. The computer-implemented method of claim 3 wherein patient events identified within the first transaction message and the second transaction message each comprise treatment data associated with treatment of a particular diagnostic condition.

5. The computer-implemented method of claim 4 wherein the patient identifying attribute comprises a risk attribute indicating that the first patient event identified within the first transaction message and the second patient event identified within the second transaction message are indicative of a risk associated with treatment of the particular diagnostic condition.

6. The computer-implemented method of claim 1 wherein the first transaction message and the second transaction message comprises at least one of a data file, a stream of data or a datagram.

7. The computer-implemented method of claim 1 wherein the de-identified patient data included within the first transaction message and the second transaction message identifies patient attributes selected from the group consisting of age, sex, address, diagnosis, specialty, diagnostic test, date of event, pharmaceutical drug prescription, and outcome of a patient event.

8. The computer-implemented method of claim 1 wherein generating the tag comprises, tagging the related patient events with an identifier.

9. A system comprising:

one or more computers and one or more storage devices storing instructions that are operable, when executed by one or more computers, to cause the one or more computers to perform operations comprising:

generating, by a server system, a user-defined matching rule, wherein:

the matching rule is expressed in a clear-text format not specific to a programming language;

the matching rule is configured to be modified by a user without modifying a programming language used to encode data stored in one or more databases of the server system, and the matching rule specifies one or more predetermined matching criteria for identifying related patient health care events from among multiple patient health care events for a plurality of patients;

receiving, by the server, a first transaction message from a first computer system, wherein:

the first transaction message includes de-identified patient data obtained from a first healthcare facility, and the first transaction message specifies a first set of patient health care events included within the de-identified patient data;

receiving, by the server system, a second transaction message from a second computer system, wherein:

the second transaction message includes de-identified patient data obtained from a second healthcare facility, and the second transaction message identifies a second set of patient health care events included within the de-identified patient data;

determining, by the server system, that a first patient event identified within the first transaction message corresponds to a patient event identified within the second transaction message based on the matching rule;

generating a custom extension to the one or more databases of the server system based on the de-identified patient data obtained from the first and second healthcare facilities;

generating, by the server system and within the custom extension to the one or more databases of the server system, a tag that associates the first patient event and the second patient event as related patient events;

appending, by the server system, the tag to a first set of data fields from the first computer system that are associated with the first patient event;

appending, by the server system, the tag to a second set of data fields from the second computer system that are associated with the second patient event;

generating, by the server system, an aggregate data record that includes (i) de-identified patient data corresponding to the first set of data fields and the second set of data fields and (ii) care pathway data linking the first set of data fields and the second set of data fields as a unique value for the related patient events; and storing, by the server system, the aggregate data record within the custom extension to the one or more databases of the server system.

10. The system of claim 9 wherein the operations further comprise:

receiving, by the server system and from a computing device of a user, a request to update at least one of the one or more predetermined matching criteria of the matching rule; and updating, by the server system, the de-identified patient data within the aggregate data record according to the at least one updated predetermined matching criteria.

11. The system of claim 9 wherein determining that the first patient event identified within the first transaction message corresponds to the second patient event identified within the second transaction message comprises:

determining a patient identifying attribute included within each of the first transaction message and the second transaction message; and determining that the first patient event identified within the first transaction message and the second patient event identified within the second transaction message correspond to the patient identifying attribute.

12. The system of claim 1 wherein patient events identified within the first transaction message and the second transaction message each comprise treatment data associated with treatment of a particular diagnostic condition.

13. The system of claim 12 wherein the patient identifying attribute comprises a risk attribute indicating that the first patient event identified within the first transaction message and the second patient event identified within the second transaction message are indicative of a risk associated with treatment of the particular diagnostic condition.

14. The system of claim 9 wherein the first transaction message and the second transaction message comprises at least one of a data file, a stream of data or a datagram.

15. The system of claim 9 wherein the de-identified patient data included within the first transaction message and the second transaction message identifies patient attributes selected from the group consisting of age, sex, address, diagnosis, specialty, diagnostic test, date of event, pharmaceutical drug prescription, and outcome of a patient event.

16. A non-transitory computer-readable medium storing software comprising instructions executable by one or more computers which, upon such execution, cause the one or more computers to perform operations comprising:
generating, by a server system, a user-defined matching rule, wherein:
the matching rule is expressed in a clear-text format not specific to a programming language;
the matching rule is configured to be modified by a user without modifying a programming language used to encode data stored in one or more databases of the server system, and
the matching rule specifies one or more predetermined matching criteria for identifying related patient health care events from among multiple patient health care events for a plurality of patients;
receiving, by the server system, a first transaction message from a first computer system; wherein:
the first transaction message includes de-identified patient data obtained from a first healthcare facility, and
the first transaction message specifies a first set of patient health care events included within the de-identified patient data;
receiving, by the server system, a second transaction message from a second computer system, wherein:
the second transaction message includes de-identified patient data obtained from a second healthcare facility, and
the second transaction message identifies a second set of patient health care events included within the de-identified patient data;
determining, by the server system, that a first patient event identified within the first transaction message corresponds to a second patient event identified within the second transaction message based on the matching rule;
generating a custom extension to the one or more databases of the server system based on the de-identified patient data obtained from the first and second healthcare facilities;
generating, by the server system and within the custom extension to the one or more databases of the server system, a tag that associates the first patient event and the second patient event as related patient events;
appending, by the server system, the tag to a first set of data fields from the first computer system that are associated with the first patient event;
appending, by the server system, the tag to a second set of data fields from the second computer system that are associated with the second patient event;
generating, by the server system, an aggregate data record that includes (i) de-identified patient data corresponding to the first set of data fields and the second set of data fields and (ii) care pathway data linking the first set of data fields and the second set of data fields as a unique value for the related patient events; and
storing, by the server system, the aggregate data record within the custom extension to the one or more databases of the server system.

17. The method of claim 1, further comprising:
providing, by the server system and for output to a client computing system, a prompt to adjust the one or more predetermined matching criteria specified by the matching rule;
receiving, by the server system and from the client computing system, a user input indicating an adjustment to a particular matching criteria from among the one or more predetermined matching criteria specified by the matching rule;
adjusting, by the server system and based on the user input indicating the adjustment to the particular matching criteria, the clear-text format of the matching rule to generate a modified matching rule; and
storing, by the server system, the modified matching rule within the one or more databases of the server system.

18. The method of claim 17, wherein the prompt is provided for output to the client computing system at a specified time point after storing the aggregate data record within the custom extension to the one or more databases of the server system.

* * * * *